US009907929B2

(12) United States Patent
Rink et al.

(10) Patent No.: US 9,907,929 B2
(45) Date of Patent: Mar. 6, 2018

(54) METHOD AND DEVICE FOR MONITORING AND TREATING SLEEP DISORDERS AND SLEEP-RELATED CONDITIONS

(71) Applicant: THE BOARD OF TRUSTEES OF THE LELAND STANFORD JUNIOR UNIVERSITY, Stanford, CA (US)

(72) Inventors: Richard Andrew Rink, Menlo Park, CA (US); Varun Boriah, San Francisco, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 208 days.

(21) Appl. No.: 14/494,275

(22) Filed: Sep. 23, 2014

(65) Prior Publication Data

US 2015/0087894 A1    Mar. 26, 2015

Related U.S. Application Data

(60) Provisional application No. 61/912,155, filed on Dec. 5, 2013, provisional application No. 62/014,441, filed
(Continued)

(51) Int. Cl.
*A61M 21/02* (2006.01)
*A61B 5/00* (2006.01)
(Continued)

(52) U.S. Cl.
CPC .......... *A61M 21/02* (2013.01); *A61B 5/4812* (2013.01); *A61B 5/1102* (2013.01); *A61B 5/1113* (2013.01);
(Continued)

(58) Field of Classification Search
CPC .............. A61M 21/02; A61M 2230/65; A61M 2021/0027; A61M 2021/0044;
(Continued)

(56) References Cited

U.S. PATENT DOCUMENTS

| | | | | | |
|---|---|---|---|---|---|
| 4,163,449 | A | * | 8/1979 | Regal | ........................ A61F 5/48 |
| | | | | | 128/886 |
| 5,865,771 | A | * | 2/1999 | Shuto | ........................ A47D 9/02 |
| | | | | | 5/904 |

(Continued)

FOREIGN PATENT DOCUMENTS

| WO | WO03/063684 A2 | 8/2003 |
|---|---|---|
| WO | WO2012/024243 A1 | 2/2012 |

(Continued)

OTHER PUBLICATIONS

Broderick et al.; Sleep terrors; The Parasomnias and Other Sleep-Related Movement Disorders; ed. By Thorpe, M.J. and Plazzi, G.; Cambridge University Press; pp. 119-120; 2010.*

(Continued)

*Primary Examiner* — Christine H Matthews
*Assistant Examiner* — Joshua D Lannu
(74) *Attorney, Agent, or Firm* — Shay Glenn LLP

(57) ABSTRACT

Methods and apparatus for monitoring, diagnosing, and treating sleep disorders such as sleep terrors are provided, which may include any number of features. One feature is an apparatus configured to partially awaken a user to treat a sleep disorder. The apparatus can include one or more sensors configured to monitor a sleep parameter of the user, one or more therapeutic devices configured to apply a therapy to the user to partially awaken the user, and an electronic controller operatively coupled to the sensors and
(Continued)

therapeutic devices to determine when to apply the therapy, and how to apply the therapy so as to only partially awaken the user.

16 Claims, 10 Drawing Sheets

Related U.S. Application Data on Jun. 19, 2014, provisional application No. 61/881,032, filed on Sep. 23, 2013.

(51) Int. Cl.
*A61M 21/00* (2006.01)
*A61B 5/11* (2006.01)

(52) U.S. Cl.
CPC .......... *A61B 5/4815* (2013.01); *A61B 5/4836* (2013.01); *A61B 5/6804* (2013.01); *A61B 5/6891* (2013.01); *A61B 5/6892* (2013.01); *A61M 2021/0016* (2013.01); *A61M 2021/0022* (2013.01); *A61M 2021/0027* (2013.01); *A61M 2021/0044* (2013.01); *A61M 2021/0066* (2013.01); *A61M 2021/0072* (2013.01); *A61M 2021/0077* (2013.01); *A61M 2021/0083* (2013.01); *A61M 2205/3375* (2013.01); *A61M 2205/502* (2013.01); *A61M 2230/06* (2013.01); *A61M 2230/10* (2013.01); *A61M 2230/42* (2013.01); *A61M 2230/65* (2013.01)

(58) Field of Classification Search
CPC .. A61M 2021/0066; A61M 2021/0072; A61M 2021/0083; A61M 2021/0016; A61M 2021/0077; A61M 2205/3375; A61M 2205/502; A61M 2230/06; A61M 2230/10; A61M 2230/42; A61M 2021/0022
See application file for complete search history.

(56) References Cited

U.S. PATENT DOCUMENTS

| | | | |
|---|---|---|---|
| 5,902,250 A | 5/1999 | Verrier et al. | |
| 6,236,621 B1 | 5/2001 | Schettino | |
| 6,505,361 B1 | 1/2003 | Ogawa | |
| 6,597,944 B1 | 7/2003 | Hadas | |
| 7,387,608 B2 * | 6/2008 | Dunlop | A61B 5/4094 600/323 |
| 7,477,144 B2 * | 1/2009 | Albert | G08B 17/00 340/506 |
| 7,749,154 B2 | 7/2010 | Cornel | |
| 7,806,831 B2 | 10/2010 | Lavie et al. | |
| 7,915,005 B2 | 3/2011 | Shaw et al. | |
| 7,942,824 B1 | 5/2011 | Kayyali et al. | |
| 2005/0190065 A1 | 9/2005 | Ronnholm | |
| 2006/0106275 A1 | 5/2006 | Raniere et al. | |
| 2008/0297357 A1 | 12/2008 | Golbin et al. | |
| 2009/0177327 A1 * | 7/2009 | Turner | A47C 21/003 700/275 |
| 2009/0210253 A1 | 8/2009 | Ash et al. | |
| 2009/0253982 A1 | 10/2009 | Wang | |
| 2010/0087701 A1 | 4/2010 | Berka et al. | |
| 2010/0206313 A1 * | 8/2010 | Peake | A61M 16/00 128/848 |
| 2011/0160543 A1 | 6/2011 | Parsey et al. | |
| 2012/0310107 A1 | 12/2012 | Doidge et al. | |
| 2013/0043988 A1 | 2/2013 | Bruno | |
| 2013/0116514 A1 | 5/2013 | Kroner et al. | |
| 2014/0046184 A1 | 2/2014 | Heinrich et al. | |
| 2014/0088378 A1 | 3/2014 | Muzet | |
| 2014/0088671 A1 | 3/2014 | Rogers et al. | |
| 2014/0371547 A1 | 12/2014 | Gartenberg et al. | |

FOREIGN PATENT DOCUMENTS

| | | |
|---|---|---|
| WO | WO2012/153263 A1 | 11/2012 |
| WO | WO2013/061185 A1 | 5/2013 |
| WO | WO2013/126557 A2 | 8/2013 |
| WO | WO2014/078593 A1 | 5/2014 |

OTHER PUBLICATIONS

Behavioral Intervention for Childhood Sleep Terrors. Durand VM, Mindell JA. Behavior Therapy 30, 705-715, 1999.*
Broderick et al.; Sleep terrors; The Parasomnias and Other Sleep-Related Movement Disorders; ed. by Thorpe, M.J. and Plazzi, G.; Cambridge University Press; pp. 119-120; 2010 (year of pub. sufficiently earlier than effective US filing and any foreign priority date).

* cited by examiner

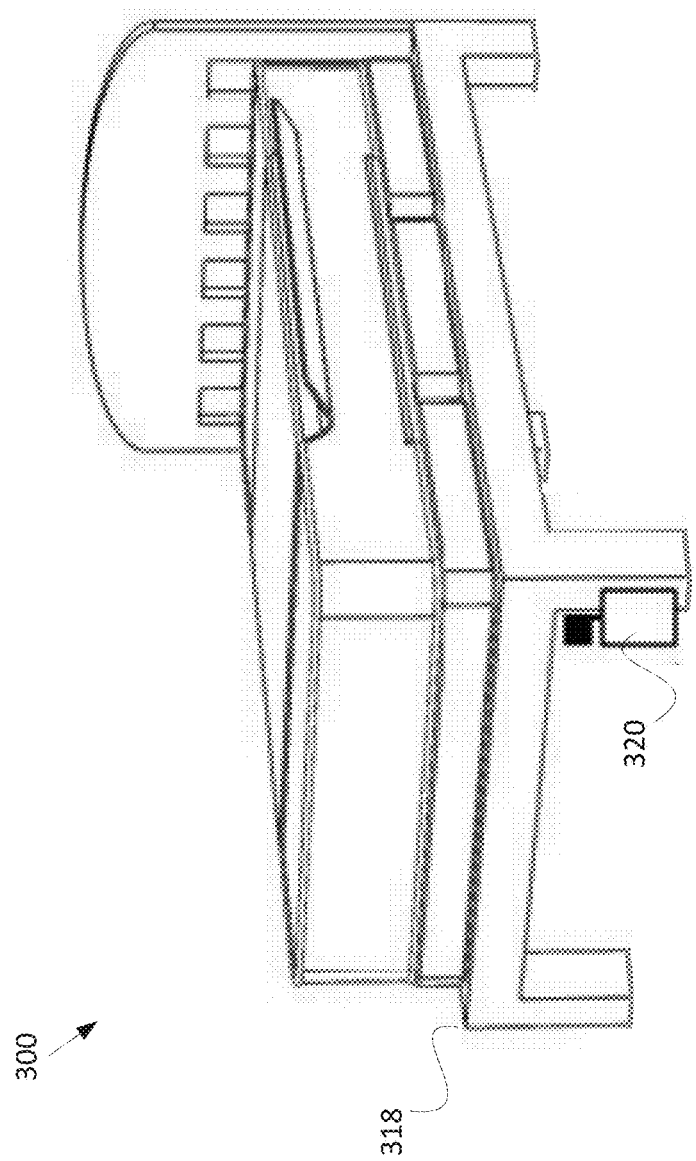

846

846

846

METHOD AND DEVICE FOR MONITORING AND TREATING SLEEP DISORDERS AND SLEEP-RELATED CONDITIONS

CROSS REFERENCE TO RELATED APPLICATIONS

This application claims the benefit of U.S. Provisional Appln. No. 61/881,032, filed Sep. 23, 2013, titled "Method and Device for Sensing Stages of Sleep Events and the Treatment of Night Terrors and Sleep Related Conditions", U.S. Provisional Appln. No. 61/912,155, filed Dec. 5, 2013, titled "Method and Device For Monitoring and Treating Parasomnias", and U.S. Provisional Appln. No. 62/014,441, filed Jun. 19, 2014, titled "Method and Device For Monitoring and Treating Sleep Disorders" all of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure is related generally to the monitoring and treatment of sleep disorders. More specifically, this disclosure relates to sensing stages of sleep and sleep events for the treatment of sleep disorders, such as night terrors.

BACKGROUND

Night terrors are a condition that affects 3 to 6% of children in the United States. The most common age groups affected by night terrors are in kids aged 1 to 9 years. Night terrors are a condition characterized by a sudden awakening from sleep, and a subsequent period of 1 to 30 minutes where the child appears to be in emotional distress but is inconsolable and cannot be fully awoken. The night terror episodes typically resolve on their own, allowing the child to fall back asleep. A child typically does not remember a night terror event in the morning following an episode. For this reason, clinical entry is distinctly different from nightmares.

Night terror episodes are generally thought to be harmless to the child, except in rare instances where the child gets out of bed or walks around engaging in activities that could lead to falls or other injuries. The condition is usually self-limiting, meaning that it will go away on its own. However, night terrors can take years to resolve on their own, usually not until a child is a teenager.

Despite the relative benign clinical course in children, night terror episodes can be very distressing to parents of the child experiencing the terrors. Parents frequently worry about the safety of their child, and they fear for their child's overall well-being given the frequent distressing awakenings. Furthermore, the night terror episodes can be very disturbing to the parent's sleep as they frequently have to awaken to tend to their child during the episodes.

When parents approach a pediatrician about night terror symptoms, typically no treatment is prescribed and the benign nature of the night terrors is explained to the parents. In special situations where treatment is needed, the child can be prescribed benzodiazepine. Another treatment option includes scheduled awakenings where the child is manually awoken by the parent prior to the occurrence of night terrors. This treatment is difficult to carry out by the parents since it is so taxing on their own sleep schedules, resulting in frequent non-compliance.

Sleep comprises two basic states: rapid eye movement (REM) sleep and non-rapid eye movement (NREM) sleep, which is made up of Stages 1 through 4. During sleep, the body cycles between REM and NREM sleep. Typically, a sleep cycle begins with a period of NREM sleep, followed by a short period of REM sleep. Dreams typically occur during REM sleep. Stage 1 sleep is the first period of light sleep, lasting for approximately 5 to 10 minutes. A person can be awakened easily during Stage 1 sleep. Stage 2 sleep is the transition between Stage 1 sleep and the deep sleep of Stages 3 and 4, typically identified by periods of muscle relaxation, slowing heart rate, and decreased body temperature. Stages 3 and 4 are the deep sleep stages. A person awakened from Stages 3 or 4 may feel disoriented or groggy. Night terrors tend to occur around the time of the transition between REM sleep and NREM sleep. NREM sleep involves the deeper stages of sleep, which includes Stages 3 and 4.

SUMMARY OF THE DISCLOSURE

In one embodiment, a method of treating sleep terrors in a user is provided, comprising the steps of determining a target treatment time based on a time of occurrence of sleep terror episodes in the user, and automatically applying therapy to the user at the target treatment time to partially awaken the user without operator intervention.

In some embodiments, the method further comprises automatically applying additional therapy to the user to fully awaken the user.

In one embodiment, the applying therapy step further comprises activating a vibrating element disposed on the user, under the user, or on a sleeping surface of the user. In another embodiment, the applying therapy step further comprises altering a topography of a sleeping surface of the user. In some embodiments, the applying therapy step further comprises changing a temperature of a sleeping environment of the user.

In one embodiment, the applying therapy step further comprises applying electrical stimulation to the user. In another embodiment, the applying therapy step further comprises applying visual stimulation to the user.

In some embodiments, the method comprises, prior to the determining step, sensing a sleep parameter of the user.

In one embodiment, the sleep parameter comprises a sleep stage of the user. In another embodiment, the sleep parameter comprises vital signs of the user. In another embodiment, the sleep parameter comprises gross or micro bodily movement of the user. In alternative embodiments, the sleep parameter comprises a sleep metric of the user.

In some embodiments, the target treatment time is determined from an average or median time of occurrence of sleep terror episodes. In another embodiment, the target treatment time is determined from an elapsed time from sleep onset to the sleep terror episodes.

An apparatus configured to improve sleep terrors in a user is provided, comprising a monitoring system configured to determine a target treatment time based on a time of occurrence of sleep terror episodes in the user, and a therapy system configured to apply therapy to the user at the target treatment time to partially awaken the user without operator intervention.

In some embodiments, the therapy system is configured to apply additional therapy to the user to fully awaken the user.

In one embodiment, the therapy system comprises at least one vibrating element disposed on the user, under the user, or on a sleeping surface of the user.

In another embodiment, the therapy system comprises at least one inflatable bladder configured to be inflated and deflated to alter a topography of a sleeping surface of the user.

In an alternative embodiment, the therapy system comprises a heating and/or cooling system configured to alter a temperature of a sleeping environment of the user.

In some embodiments, the therapy system comprises a visual stimulating device configured to stimulate the user's eyes.

In one embodiment, the target treatment time is determined from an average or median time of occurrence of sleep terror episodes. In another embodiment, the target treatment time is determined from an elapsed time from sleep onset to the sleep terror episodes.

In some embodiments, the monitoring system is configured to monitor a sleep parameter of the user to determine the target treatment time.

A method of partially awakening a user is also provided, comprising the steps of determining a target awakening time based on a time of occurrence of sleep events in the user, and automatically applying an intervention to the user at the target awakening time to partially awaken the user without operator intervention.

In one embodiment, applying the intervention to the user comprises applying vibration stimulation to the user. In another embodiment, applying the intervention to the user comprises applying electrical stimulation to the user. In an additional embodiment, applying the intervention to the user comprises applying temperature stimulation to the user. In further embodiments, applying the intervention to the user comprises applying visual stimulation to the user.

A method of partially awakening a user to treat a sleep disorder is provided, comprising the steps of determining a target awakening time, automatically applying an intervention to the user at the target awakening time without operator intervention, monitoring a sleep state of the user while applying the intervention, and terminating the intervention automatically when the monitoring of the sleep state indicates that the user is partially awakened.

In one embodiment, applying the intervention to the user comprises applying vibration stimulation to the user. In another embodiment, applying the intervention to the user comprises applying electrical stimulation to the user. In an additional embodiment, applying the intervention to the user comprises applying temperature stimulation to the user. In further embodiments, applying the intervention to the user comprises applying visual stimulation to the user.

An apparatus configured to partially awaken a user to treat a sleep disorder is provided, comprising a monitoring system configured to sense a sleep parameter of a user to determine a target awakening time to treat the sleep disorder, and an intervention system configured to apply a therapeutic intervention to the user at the target awakening time to partially awaken the user without operator intervention.

A method of partially awakening a user to treat a sleep disorder is provided, comprising the steps of sensing a sleep parameter of the user, determining a target awakening time based on the sensed sleep parameter, automatically applying an intervention to the user at the target awakening time without operator intervention, monitoring a sleep state of the user while applying the intervention, and terminating the intervention automatically when the monitoring of the sleep state of the user indicates that the user is partially awakened.

In some embodiments, the sleep parameter comprises a sleep stage of the user. In another embodiment, the sleep parameter comprises vital signs of the user. In one embodiment, the sleep parameter comprises gross or micro bodily movement of the user. In some embodiments, the sleep parameter comprises a sleep metric of the user.

In one embodiment, the automatically applying an intervention step further comprises activating a vibrating element disposed on the user, under the user, or on a sleeping surface of the user. In another embodiment, the automatically applying an intervention step further comprises altering a topography of a sleeping surface of the user. In some embodiments, the automatically applying an intervention step further comprises changing a temperature of a sleeping environment of the user. In another embodiment, the automatically applying an intervention step further comprises applying electrical stimulation to the user. In an additional embodiment, the automatically applying an intervention step further comprises applying visual stimulation to the user.

An apparatus configured to partially awaken a user is also provided, comprising at least one sensor configured to monitor a sleep parameter of the user, at least one therapeutic device configured to apply a therapy to the user to partially awaken the user, and a controller operatively coupled to the at least one sensor and the at least one therapeutic device, the controller configured to determine a target awakening time based on the monitored sleep parameter and to control the at least one therapeutic device to apply the therapy to the user at the target awakening time to partially awaken the user.

In one embodiment, the at least one sensor comprises a force sensor. In another embodiment, the at least one sensor comprises a motion sensor. In another embodiment, the at least one sensor comprises a heart rate sensor. In some embodiments, the at least one sensor comprises an audio sensor.

In other embodiments, the at least one therapeutic device comprises a vibrating element. In another embodiment, the at least one therapeutic device comprises an electrical stimulator. In an additional embodiment, the at least one therapeutic device comprises a cooling and/or heating system configured to alter a temperature of a sleep environment of the user. In one embodiment, the at least one therapeutic device comprises a visual stimulating device. In another embodiment, the at least one therapeutic device comprises an auditory device. In a further embodiment, the at least one therapeutic device comprises a mechanism configured to alter a topography of a sleeping surface of the user.

In one embodiment, the controller is further configured to determine a sleep state of the user while the at least one therapeutic device applies the therapy to the user, and the controller is further configured to terminate the therapy when the user is partially awakened.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 3 shows another embodiment of a sleep monitoring and therapeutic system.

DETAILED DESCRIPTION

Figure 1:
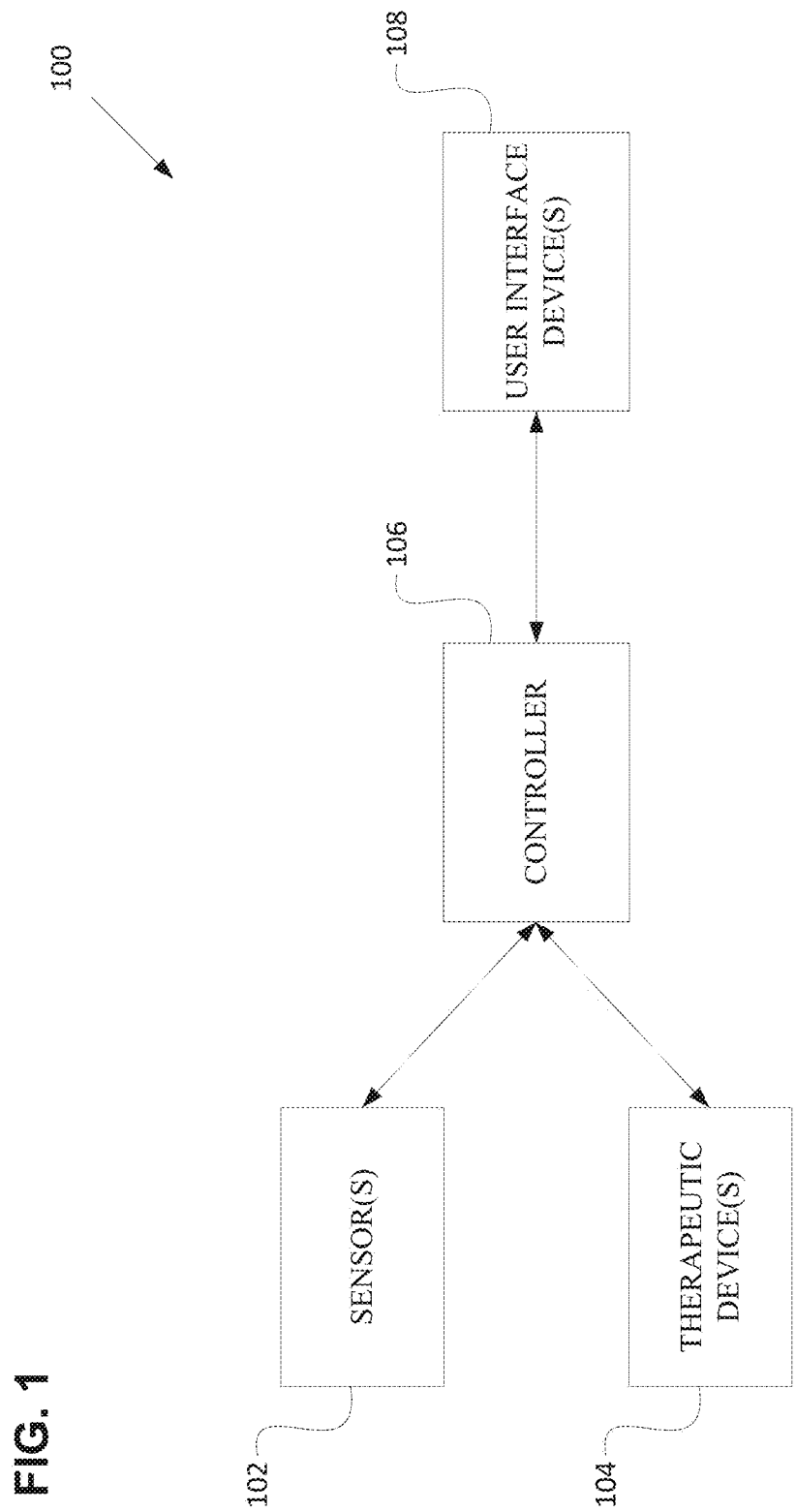
FIG. 1 is a schematic diagram of a sleep monitoring and therapeutic system.

The following description outlines various embodiments of systems, devices and methods for monitoring the sleep habits and sleep stages of the user, detecting the occurrence of sleep disorder episodes, and treating the sleep disorders. In various alternative embodiments, the systems, devices and methods may be altered, combined or otherwise changed, without departing from the scope of the invention.

The present disclosure describes systems, devices and methods for monitoring the sleep habits, sleep metrics, and sleep stages of a user, detecting the occurrence of sleep disorder episodes, and treating the sleep disorders. In some embodiments, the sleep disorder to be treated can be night terrors. The present disclosure provides devices and methods for precisely timed awakenings from sleep to treat a number of sleep-related disorders, including the treatment and/or improvement of night terrors, bedwetting, sleepwalking, sleep apnea, low-grade sleep apnea, positional sleep apnea, snoring, adult enuresis, RLS, frequent night awakenings and SIDS, amongst other conditions. This disclosure addresses several shortcomings with prior attempts to treat sleep disorders.

This disclosure provides systems and methods for determining the state or stage of sleep of a user, e.g., determining in real-time what sleep stage a user is in. This disclosure also provides systems and methods for determining when a sleep event occurs or is likely to occur, e.g., determining what time a user is likely to have a sleep terror event. This disclosure also provides methods and apparatus configured to disrupt a certain sleep stage to awaken or partially awaken a user.

Sleep terrors tend to occur around the time of NREM sleep, which involves the deeper stages of sleep, including Stages 3 and 4. In the present disclosure, methods and devices are described that are configured to detect the specific sleep stage that a user or patient is in. Furthermore, devices and methods are described that can detect at what time a sleep terror or other sleep event is occurring or is likely to occur. Sleep terrors classically occur at similar times each night after sleep onset and during similar stages of sleep each night for a specific individual. The methods and devices described herein include many different embodiments to detect which stage of sleep a sleep terror or sleep event is happening, or at what time of night or into a sleep cycle that a sleep terror or sleep event is happening.

Methods and devices are also described herein that are configured to awaken or partially awaken a user prior, during, or after to a sleep event.

The present disclosure also describes systems and methods for applying a therapy to the user to awaken or partially awaken the user. This therapy can be tailored and suited to treat, reduce, or eliminate the occurrence of sleep disorders, such as night terrors. In some embodiments, the therapy can be applied directly to the user. In other embodiments, the therapy can adjust or change a sleeping environment of the user. The therapeutic element(s) of the present disclosure can be worn by or placed on the user, incorporated into a bed, mattress or bedding materials, or be separate from the user and the sleeping environment.

FIG. 1 is a schematic diagram illustrating one embodiment of a sleep monitoring and therapeutic system 100. The system can generally comprise one or more sensors 102, one or more therapeutic devices 104, an electronic controller 106 configured to communicate with and control the sensor(s) 102 and therapeutic device(s) 104, and one or more user interface devices 108 configured to display system parameters, settings, and alerts to a user and also receive input from the user regarding the operation of the system. In some embodiments, one or more of the components described above can be integrated into a single device. For example, a smartphone, tablet, or personal computer can include the electronic controller and user interface device components, and can be configured to remotely control the therapeutic device(s) and receive information from the sensor(s).

The sensor(s) 102 can be operatively connected to the controller 106 for the detection of the sleep stage or state of the user, detection of sleep metrics, detection of either gross or micro bodily movement, and/or detection and monitoring of user vitals such as heart rate, body temperature, blood pressure, etc. The one or more therapeutic device(s) 104 can also be operatively connected to and controlled by the controller 106 to selectively apply the desired therapy to the user. In some embodiments, the system 100 can include on or more user interface device(s) including a display and a user input interface (e.g., a keyboard, touch screen, or voice activation mechanism). The user interface device(s) 108 can comprise, for example, a personal computer, tablet, or smartphone.

The schematic diagram of FIG. 1 is shown for illustrative purposes only to describe the main components of a sleep monitoring and therapeutic system. It should be understood that the sensor(s), therapeutic device(s), controller, and/or user interface device(s) can be integrated into a single module or apparatus for the detection, monitoring, and treatment of various sleep disorders.

Specifics on the type and placement of individual components of the sleep monitoring and therapeutic system will now be described. In some embodiments, the sleep monitoring and therapeutic system of FIG. 1 can be completely external to the user, can be worn by the user, or can be implanted inside the user. The sleep monitoring and therapeutic system can also be integrated into or place within, near, or adjacent to a sleeping environment of the user, such as a mattress, bed frame, bedding, or clothing of the user. Embodiments for each principle are described in detail below. It is important that the sleep monitoring and therapeutic system be positioned in proximity to the user so as to awaken or partially awaken the patient or user when therapy is applied by the therapeutic device(s).

Figure 2B:
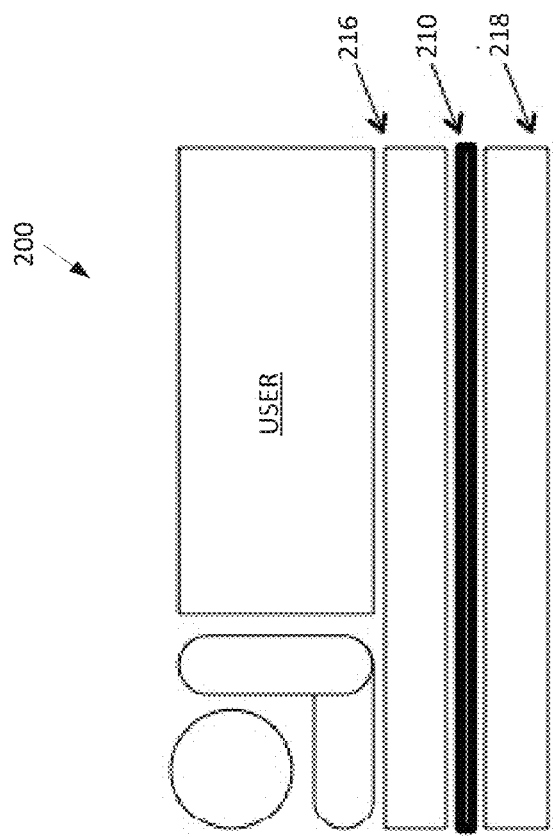
FIGS. 2A-2B show one embodiment of a sleep monitoring and therapeutic system.
Figure 2A:
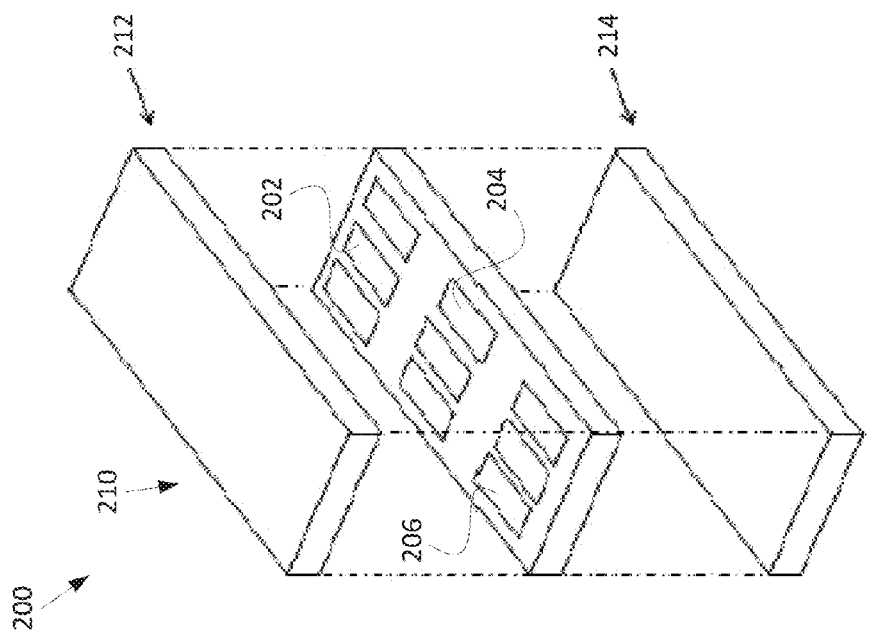

FIGS. 2A-2B show one embodiment of a sleep monitoring and therapeutic system 200 comprising one or more sensors 202 and one or more therapeutic devices 204 integrated into a mattress pad 210. FIG. 2A is an exploded view of the sensor(s), therapeutic device(s), and a controller 206 sandwiched between a top padding layer 212 and a bottom padding layer 214 of the mattress pad 210. The top padding layer 212 of the mattress pad 210 can be soft to improve comfort for the user, and can comprise latex foam, HDPE foam, spring box, feather padding, or any other material that promotes comfort and flexibility. The bottom padding layer 214 of the mattress pad can be more rigid in order to aid the detection functions of the sensor(s), particularly if the sensors are motion sensors. The bottom padding layer can provide support to the mattress pad and can comprise, for example, latex foam, HDPE foam, a box-spring, feather padding, or any other material that promotes comfort and flexibility.

In some embodiments, the controller 206 can be external to the mattress pad, or alternatively, the controller can be integrated into the sensor(s) or therapeutic device(s) themselves to reduce the number of components placed into the mattress pad. Referring to FIG. 2B, the sleep monitoring and therapeutic system 200 is shown integrated into a mattress pad 210, which can be placed on or under a mattress 216, which in turn may be placed within a bed frame 218, crib, or on the ground. The user can lie and sleep upon the mattress pad 210 during use of the sleep monitoring and therapeutic system.

In one embodiment, shown in FIG. 3, the sleep monitoring and therapeutic system can 300 be placed on or be integrated into a bed frame 318. In the illustrated embodiment, the sleep monitoring and therapeutic system 300 comprises a sleep monitoring and therapy module 320 that combines one or more sensors, therapeutic devices, and/or controllers into a single housing that can be placed in proximity to the user or attached to something in proximity to the user. In some embodiments, the sleep monitoring and therapy module includes all the components of a sleep monitoring and therapeutic system including sensor(s), therapeutic device(s), and a controller, and in other embodiments the module may include only sensor(s), or therapeutic device(s) and the other components can be separate. Here, the sleep monitoring and therapy module 320 is shown attached to a leg of the bed frame 318. The module can be attached or connected to a desired piece of furniture, flooring, walls, ceiling with adhesive, screws or nails, straps, snaps, buckles, Velcro, or the like.

Figure 4A:
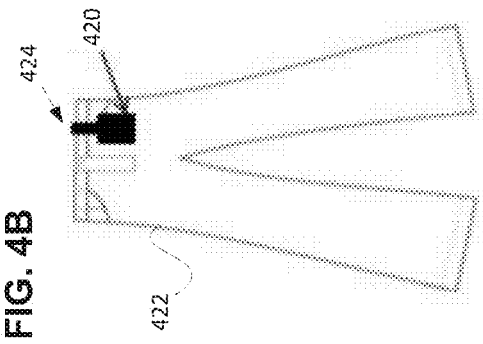
FIGS. 4A-4D illustrate embodiments of a sleep monitoring and therapeutic system that can be integrated into clothing of the user.
Figure 4B:
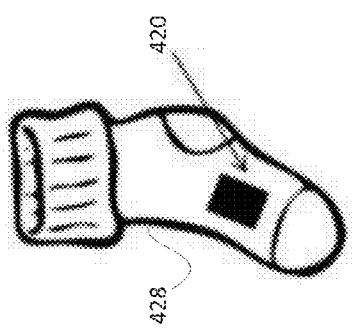
Figure 4C:
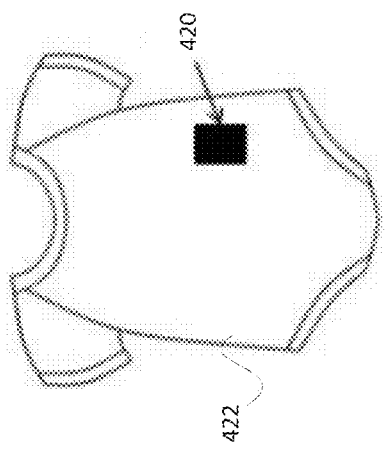
Figure 4D:
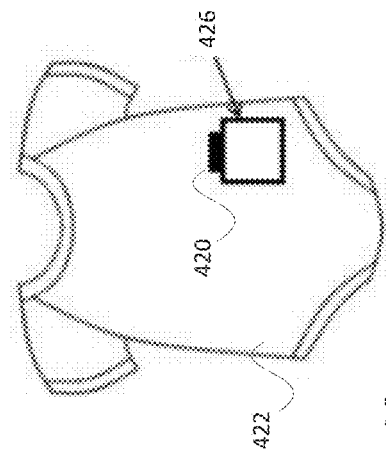

In addition to placing the sleep monitoring and therapeutic system on or near a sleeping surface of the user, other embodiments of the sleep monitoring and therapeutic system provide configurations that can be worn by the user. In FIG. 4A, a sleep monitoring and therapy module 420 can be integrated into a clothing garment 422. If the user is a child, the garment can be a child's or infant's clothing such as pajamas, a onesie, shirts, shorts, pants, caps, beanies, diapers, etc. The module can be, for example, stitched or adhered to the garment, attached with mechanical fasteners, or placed between layers of fabric. In FIG. 4B, a sleep monitoring and therapy module 420 can be attached to a clothing garment 422, such as with a belt clip 424. In FIG. 4C, a sleep monitoring and therapy module 420 can be secured within a pocket 426 of a garment 422. In another embodiment, shown in FIG. 4D, the sleep monitoring and therapy module 420 can be incorporated in to a sock 428 to be worn by the user. The protruding parts of the device may be placed on the sole of the foot so that it does not interfere with sleep, as the user will not lie on that surface of the body, and where there may be a higher density of sensory receptors.

In the wearable embodiments described above, the module can include one or more of the system components described above. For example, the sleep monitoring and therapy module can include only a sensor, only a sensor and a therapeutic device, or can include one or more of all components such as one or more sensors, therapeutic devices, and controllers.

Figure 5:
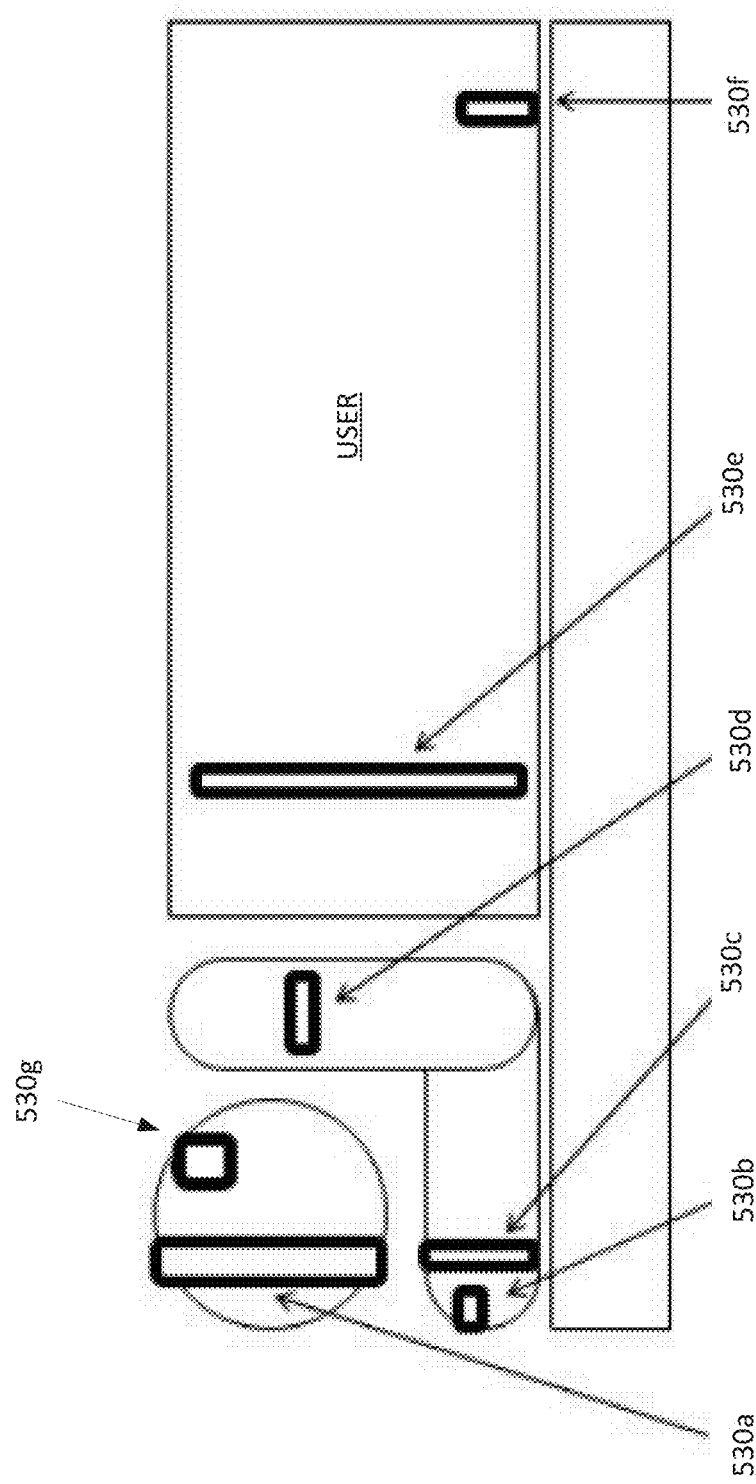
FIG. 5 shows wearable embodiments of the sleep monitoring and therapeutic system.

In another embodiment, shown in FIG. 5, sleep monitoring and therapy module can be incorporated into various types of wearable articles 530*a-f*. For example, the wearable article can be in the form of a band worn on the head (530*a*), finger (530*b*), wrist (530*c*), arm (530*d*) chest (530*e*), or leg/foot/ankle (530*f*). The wearable article can be, for example, a band or strap that holds or supports the sleep monitoring and therapy module(s) described above. Furthermore, the sleep monitoring and therapy module can be incorporated into bedding materials, such as sheets or blankets. Alternate embodiments may incorporate the sleep monitoring and therapy module into a stuffed animal, teddy bear, pacifier, ingestible tablet/capsule, or other item typically held by the user during sleep.

In another embodiment, the sleep monitoring and therapy module can be placed directly on the patient or user, indicated by 530*g*, so as to be in contact with the mastoid process, forehead, cranial bones, or between the teeth. Placing the module directly on the patient or user, particularly on the head, can take advantage of vibrations conducted from the skull bones.

The present disclosure describes methods and devices configured to detect a sleep stage or sleep state that a user is in. As part of this, the methods and devices described herein can also be configured to detect at what time into a sleep cycle a night terror or other sleep event occurs and/or is likely to occur in the future. Night terrors classically occur at similar times each night after sleep onset and during similar stages of sleep each night for an individual user. The method and devices described herein entail many different embodiments to detect during what stage of sleep a sleep event such as a night terror is happening or at what time of night a sleep event such as a night terror is happening.

As described above, a sleep monitoring and therapeutic system can include one or more sensors, one or more therapeutic devices, and an electronic controller operatively coupled to the sensor(s) and therapeutic device(s). In one embodiment, the sensor(s) of the sleep monitoring and therapeutic system can be used during a baseline period to determine a time of sleep onset, a time of occurrence of sleep events such as sleep terror episodes each night, an elapsed time from sleep onset to the sleep event such as a night terror episode, and the frequency of occurrence of sleep events such as night terror episodes. In some situations, this baseline monitoring period can extend up to 6 months, during which, no treatment of the sleep events is administered.

At the end of the baseline monitoring period, the sleep monitoring and therapeutic system can be configured to determine a target treatment time, treatment frequency, the efficacy of the therapeutic intervention, or any combination thereof. The sleep monitoring and therapeutic system can also be used to determine a satisfactory end point for the therapeutic intervention. For example, the electronic controller can evaluate the data collected by the sensor(s) and determine a target treatment time, treatment frequency, efficacy of the therapeutic intervention, and end point for therapeutic intervention.

In some embodiments, the target treatment time can be determined based on the pattern of the time of occurrence of sleep event (such as night terror episodes) each night, and/or the elapsed time from sleep onset to the sleep event (such as night terror episodes). In one embodiment, the target treatment time can be determined from the average or median time of occurrence of sleep events (such as night terror episodes) and/or the elapsed time from sleep onset to the sleep event (such as night terror episodes). In some embodiments, the target treatment time is determined such that it occurs before the typical time of occurrence of sleep events (such as night terror episodes). The target treatment time can precede the typical time of occurrence of a sleep event by approximately 1 minute to 60 minutes.

Once the target treatment time is determined, the therapeutic device(s) of the sleep monitoring and therapeutic system can be used to administer therapeutic intervention to the user to treat the occurrence of sleep events, such as night terrors. In some embodiments, the duration of each administration of the therapeutic intervention can extend between 1 second and 30 minutes. In other embodiments, the therapeutic intervention is not applied based on a set time period, but is instead applied based on the wakefulness of the patient or user. For example, the therapeutic device(s) can be configured to apply therapeutic intervention to the user until the user is partially awakened, or alternatively, until the user is fully awakened. This will be discussed in more detail below.

The sleep monitoring and therapeutic system can administer therapeutic intervention for a therapy period of up to 6 months or more, which is referred to as the period of therapeutic intervention. In some embodiments, the sleep monitoring and therapeutic system can administer therapeutic intervention every night during the period immediately after the baseline monitoring period. The frequency of the therapeutic intervention can be reduced over time, decreasing from 7 days/week to 0 days/week, at an appropriate rate. In one embodiment, the frequency of the therapeutic intervention can be increased or decreased based on the frequency of occurrence of sleep events.

In one embodiment, directed specifically to the treatment of night terror episodes, the sleep monitoring and therapeutic system can perform therapeutic intervention nightly until the user successfully goes a pre-determined period without a sleep terror episode, such as 7 days without a sleep terror episode. If the user achieves this level of success, the frequency of therapeutic intervention can be reduced. For example, the therapeutic intervention can be reduced by 1 night per week for each subsequent week without a sleep terror episode. If the user has a sleep terror episode during this time period, then the therapeutic intervention frequency can be reset to include therapy more frequently, or fully reset to 7 nights/week. The frequency of therapeutic intervention of can be decreased until the user no longer experiences sleep terror episodes during the night.

In some embodiments, the target treatment time and/or the treatment frequency can be modified in real-time during the therapeutic intervention period. For example, the controller of the sleep monitoring and therapeutic system can be configured to automatically decrease the frequency or treatment time of therapeutic intervention based on data collected by the sensor(s). The sensors can be configured to identify sleep events, or the lack thereof, and that information can be used by the controller to further optimize the therapy.

The sensors of the sleep monitoring and therapeutic system can comprise of one or more sensors that are capable of detecting, sensing, and collecting data relating to a number of user and sleep-related parameters. For example, the sensor(s) of the present disclosure can be configured to sense and detect a variety of sleep metrics and user vitals. The detected, sensed, and/or collected data can be used by the controller to control the therapy applied to the user by the therapeutic device(s) of the sleep monitoring and therapeutic system.

In one embodiment, the sensors of the sleep monitoring and therapeutic system are configured to determine sleep metrics including, but not limited to, a lights-out time, a lights-on time, a time of sleep onset, a total sleep time, a wake after sleep onset, a sleep period time, sleep latency, etc. Lights-out time can be the start of sleep recording. Lights-on time can be the end of sleep recording. Time of sleep onset can be the time that the user falls asleep. Total sleep time can be the minutes of sleep spent in Stages 1, 2, 3, 4, and REM. Wake after sleep onset can be the minutes that a user is awake after first sleep but before the final awakening (e.g., before the user awakens for the day). Sleep latency can be the time from lights-out until the first epoch of sleep.

Some or all of the sensor(s) described herein can be configured to monitor attributes of sleep including gross body movement, heart rate, heart rate variability, respiratory rate, respiratory rate variability, body temperature, ambient room temperature, light levels, EKG signals, EEG signals, sound, etc. The sensors can aid with the diagnosis of sleep disorders or conditions. For example, the sensors may monitor the user's sleep pattern to generate data that can be used to diagnose sleep disorders. The data generated can be communicated to a certified professional in order to make the diagnosis, or the controller can determine a diagnosis.

In a preferred embodiment, the sensor(s) can be located in various positions on or under a mattress, so that at least one sensor can be placed under the torso of the user, even if the user moves during sleep, to improve the ability to measure vital signs such as respiratory rate and heart rate. The sensor(s) can be configured to collect data from the user relating to a wakefulness of the patient or user. The sleep monitoring and therapeutic system can therefore utilize the sensor(s) to differentiate sleep events such as sleep terrors from other reasons for night awakenings, such as the need to go to the bathroom, leaving to go to the parent's room, enuresis, hunger, habitual night waking, etc. For example, a lack of any gross body movement may indicate that the user is fully asleep. Similarly, a short duration of gross body movement (e.g., body movement for 1 to 3 seconds) may indicate that the user is partially awake, and gross body movement enduring longer than 3 seconds may indicate that the user has fully awoken. Similarly, changes in heart rate or respiratory rate can indicate the wakefulness of the user, as can sounds made by the user.

All of the sensors described herein can be placed on the mattress or beneath the mattress, as shown in FIGS. 2A-2B, on a bed frame or near the user, as shown in FIG. 3, incorporated into on clothing, as shown in FIGS. 4A-4D, or as a wearable article or directly on the user, as shown in FIG. 5.

Many different types of sensors can be used to acquire the sleep metrics and user vitals data described above. In one embodiment, the sensor(s) of the sleep monitoring and therapeutic system can be force sensors, such as a piezoelectric force sensor. A sleep monitoring and therapeutic system utilizing a force sensor can incorporate the force sensor into a situation in which the user is lying atop the sensor during sleep. For example, force sensors can be incorporated into the mattress pad configuration illustrated in FIGS. 2A-2B.

In another embodiment, the sensor(s) of the sleep monitoring and therapeutic system can be motion sensors. The motion sensors can comprise, for example, infrared motion detection sensors, accelerometers, cameras, gyroscopes, light sensors, or vibration sensors. In some embodiments, the motion sensors can be capable of measuring motion or movement along multiple axes.

In another embodiment, the sensor(s) of the sleep monitoring and therapeutic system can be heart rate sensors. The heart rate sensors can comprise, for example, acoustic heart rate sensors or pulse oximetry sensors, or Ballistocardiography (BCG) sensors. BCG sensors utilize a technique of measuring the ballistic forces of the heart in order to capture the repetitive motions of the human body arising from the sudden ejection of blood into the greater vessels with each heartbeat. The ballistic forces and the resultant movement generated is typically along the craniocaudal axis. Sensors used for BCG are typically oriented along the craniocaudal axis of the user, which in most cases would align with the axis from the head of the bed to the footboard. Most users shift around during sleep and as a result, the measurement axis of BCG sensors may not align with the craniocaudal axis of the user. This is especially true for children who toss and turn during sleep and can often be found flipped over in bed. In one embodiment, the sensors are configured to measure forces and acceleration along multiple axes enabling the use of BCG when a single measurement axis of the sensor is not aligned with the craniocaudal axis of the user.

In another embodiment, the sensor(s) of the sleep monitoring and therapeutic system can be configured to monitor the autonomic nervous system. In some embodiments, sensors can be included to monitor the autonomic nervous system through skin conductivity, sweat, body temperature, gastrointestinal motility, pupil dilation, heart rate, heart rate variability, electrocardiography, blood pulse transit time, or any combination thereof.

In yet another embodiment, the sensor(s) of the sleep monitoring and therapeutic system can be audio sensors configured to detect sounds made by the user, such as crying, screaming, mumbling, and/or talking. These audio sensors can be, for example, microphones.

The present disclosure also provides a sleep monitoring and therapeutic system having one or more therapeutic devices configured to awaken or partially awaken a user in response to a sleep event, or prior to the occurrence of a sleep event. The therapeutic device(s) can be controlled by the electronic controller of the sleep monitoring and therapeutic system, and can be used in conjunction with the sensor(s) and the data collected by the sensors.

The sleep monitoring and therapeutic system, utilizing the sensors and therapeutic devices described herein, can be configured to shift sleep stages of the user prior to the onset a sleep event such as a sleep terror. All of the therapeutic devices described herein can be placed on the mattress or beneath the mattress, as shown in FIGS. 2A-2B, on a bed frame or near the user, as shown in FIG. 3, incorporated into on clothing, as shown in FIGS. 4A-4D, or as a wearable article or directly on the user, as shown in FIG. 5.

The sleep monitoring and therapeutic system can include features that awaken or partially awaken the user and then allow the user to go back to sleep at a time period in relation to a sleep event, such as night terrors, sleep walking, frequent night awakenings, sleep apnea, etc. A reasoning behind the described function is to perform the principle of scheduled awakenings. In one embodiment, the sleep monitoring and therapeutic system can automatically (without intervention by others) apply therapeutic intervention to awaken or partially awaken the user. The application of therapeutic intervention can be in response to information collected by sensors of the system (e.g., user vitals, user bodily movement, user sleep state, etc.). In another embodiment, the sleep monitoring and therapeutic system can be manually set or programmed to apply therapeutic intervention at a specific time, much like an alarm clock.

When using scheduled awakenings as a therapy for night terrors, the time of night terrors can be sensed and recorded by the sleep monitoring and therapeutic system during several consecutive nights, and the system can apply therapeutic intervention to awaken or partially awaken the user just prior to the typical time of night terrors. This intervention can interrupt the natural process of night terror development and prevent the night terror from happening again in the future. In one embodiment, the goal of the present disclosure is to automate this process so that no human interaction or intervention is required to complete the treatment. Thus, the system of the present disclosure can comprise a closed-loop, feedback based system which the electronic controller alters or adjusts therapeutic intervention applied to the user based on data collected by the sensors.

In one embodiment, the end point for the therapeutic intervention by the sleep monitoring and therapeutic system is a partial awakening or a full awakening from sleep for the user. In another embodiment, the end point for the therapeutic intervention is gross body movement. Specifically, gross body movement can be a sufficient end point for obstructive sleep apnea, positional sleep apnea, snoring, partial awakening, etc.

The sleep monitoring and therapeutic system can be capable of differentiating between a normal awakening and/or arousal and an awakening and/or arousal due to a sleep disorder. For example, a gradual increase in autonomic response such as heart rate, respiratory rate, etc. can be indicative of a normal awakening and/or arousal. An acute increase in autonomic response can be indicative of an awakening and/or arousal due to a sleep disorder.

Two types of partial awakenings (also called partial arousals, nonsustained awakenings, or nonsustained arousals) from sleep are known: EEG arousals and clinical arousals. Both of these partial awakenings occur after at least 10 seconds of sleep, often confirmed by polysomnography. EEG arousals can occur with any shift in EEG frequency to alpha or theta regardless of submental EMG changes during NREM sleep, or with submental EMG changes during REM sleep. Clinical arousals can occur when there is gross body movement or vocalization in response to an arousal stimulus.

When a partial awakening is sustained, it is termed a full awakening from sleep. A full awakening, in addition to being a sustained awakening, will be accompanied by the person being able to perform conscious, awake behaviors. Partial and full awakenings are associated with autonomic activations as described below.

Autonomic activation, or simply activation, is a state of lesser "wakefulness" than a partial or full awakening. This can be signaled by one or a combination of heart rate changes, heart rate variability, pulse rate variability, respiratory rate changes, or skin galvanic response changes. Autonomic activation indicates sub-cortical activation in the brain, while partial awakenings and full awakenings indicate cortical activation.

Awakening can be seen as a continuum from asleep to awake. On that continuum, in order from asleep to awake, would be asleep, followed by activation, followed by partial arousal, followed by full awakening.

By partially awakening/arousing the user, the system facilitates the return to sleep at the end of the therapeutic intervention and reduce the time of lost sleep. Further, when used in children, a complete arousal/awakening may result in the child looking for a parent, crying or being disoriented. A partial arousal/awakening may be less likely to be remembered when the user awakes from sleep in the morning.

Figure 6A:
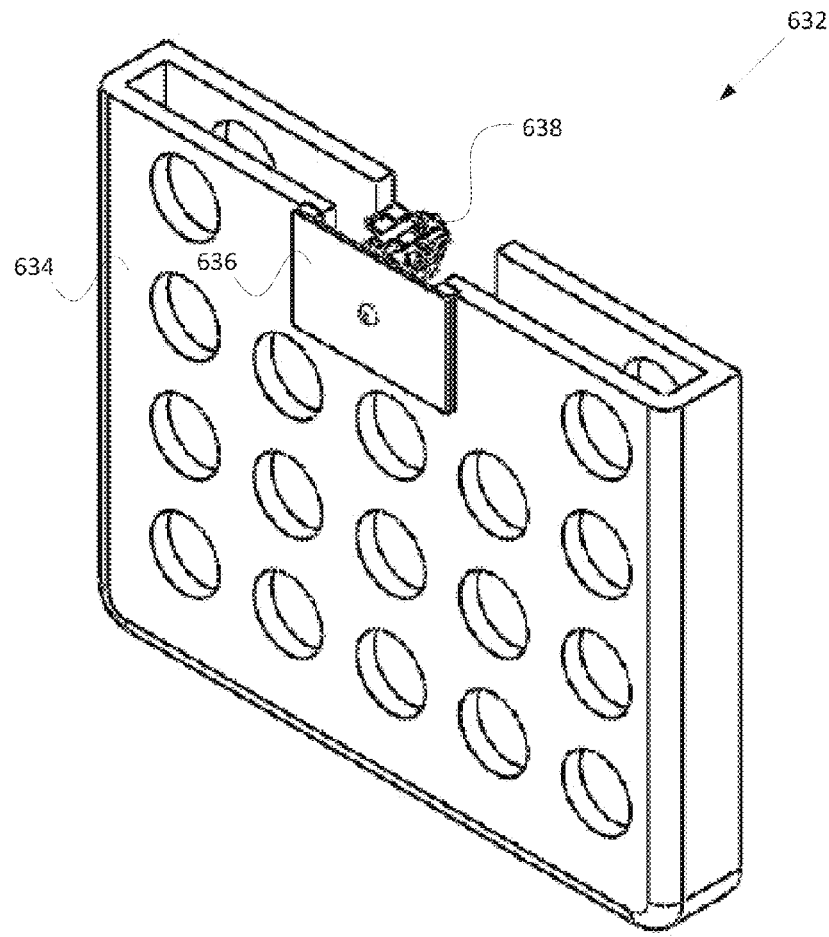
FIGS. 6A-6B show one embodiment of a therapeutic device comprising a vibration element.
Figure 6B:
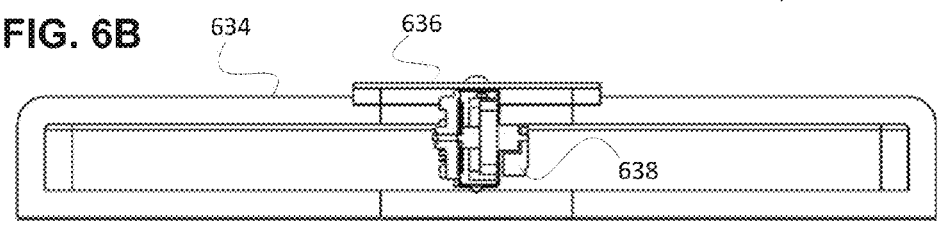

In one embodiment, the therapeutic device(s) can comprise one or more vibrating elements that generate a vibrotactile stimulus to awaken or partially awaken the user. Referring to FIG. 6A (perspective) and FIG. 6B (top-down), a therapeutic device comprising a vibrating element 632 can include a housing 634, a vibrating plate 636, a vibrating motor 638, and features for fastening the various components of the device. The vibrating motor can comprise of a motor with an eccentric mass. The vibrating motor can be attached to the vibrating plate through various fastening mechanisms including but not limited to a sheet metal clamp, bolts, adhesives etc. The vibrating plate and motor can be attached to the housing. In other embodiments, the vibrotactile stimulus can be generated with a non-rotating vibrating element including but not limited to a linear resonance actuator.

Figure 6C:
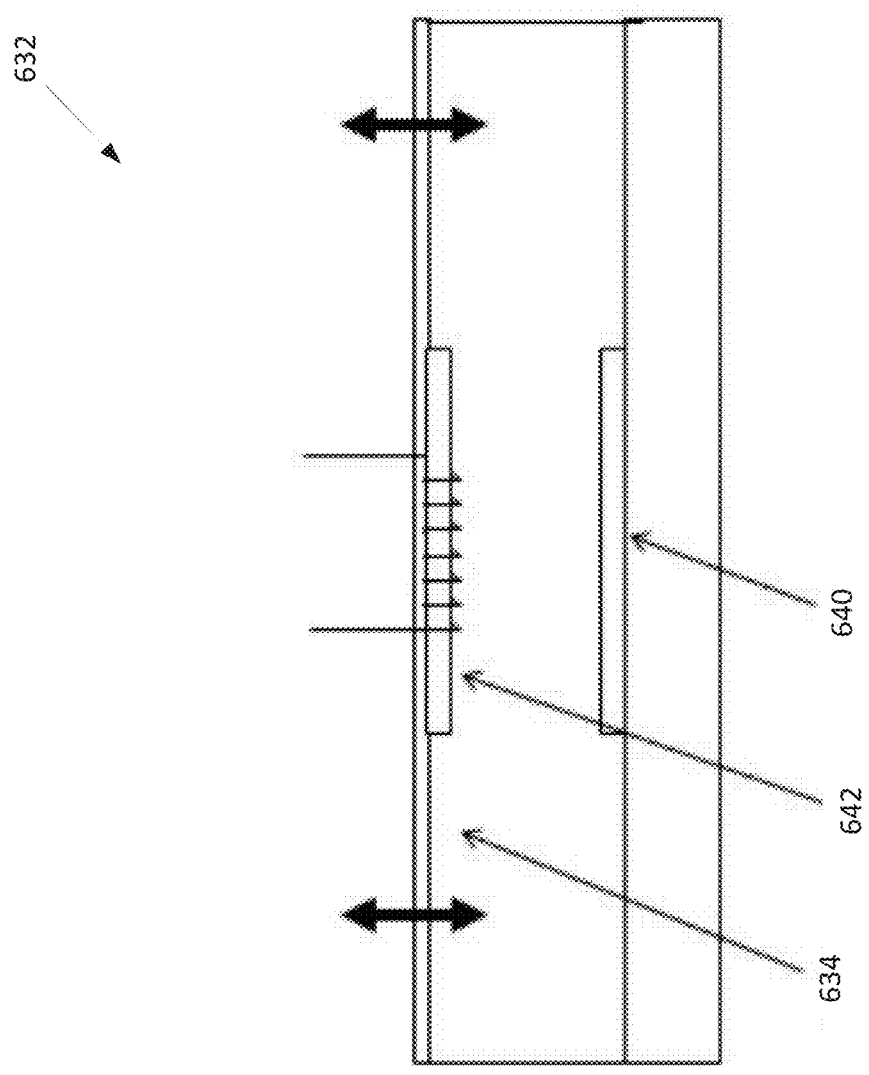
FIG. 6C shows another embodiment of a vibration element.

Referring to FIG. 6C, one embodiment of a vibrating element 632 can comprise one or more permanent magnets 640 and electromagnets 642 disposed in the housing 634. The electromagnet is placed in the proximity of the permanent magnet. Either the permanent magnet or the electromagnet can be fixed firmly into position whereas the other can be mobile or not firmly fixed in place. Electricity can be delivered through a coil of the electromagnet to rapidly change a direction of the magnetic field. This causes the permanent magnet to oscillate between being attracted to and being repelled from the electromagnet, causing it to vibrate back and forth and create a vibration within the housing.

In some embodiments, the vibrating plate can be recessed within a housing to ensure that the vibrating plate is not collapsed due to the weight of the mattress and/or the user. This configuration ensures that under application of the weight of the mattress and/or the user, the vibrating plate is able to oscillate and propagate the vibrations to the mattress and/or the user. Further, the vibrating plate can be located above the surface of the housing in order to positively bias the vibrating plate toward the mattress. This can ensure consistent contact between the vibrating plate and the mattress.

In some embodiments, the therapeutic device of the sleep monitoring and therapeutic system is configured to preferentially direct the vibrations to the location of the user. Since the user can move around in bed over the course of the night, directional application of the vibration ensures that the required vibration intervention is delivered to the user. Furthermore, directional vibration can be beneficial in situations where multiple persons share the same bed or sleeping situation. In some embodiments, the vibration element(s) are configuration to create a uniform vibration across the surface of the mattress. Furthermore, vibration intensity can be adjusted or automatically determined by the system to maintain vibration above a specific threshold irrespective of the user's relative location on the bed.

Figure 7:
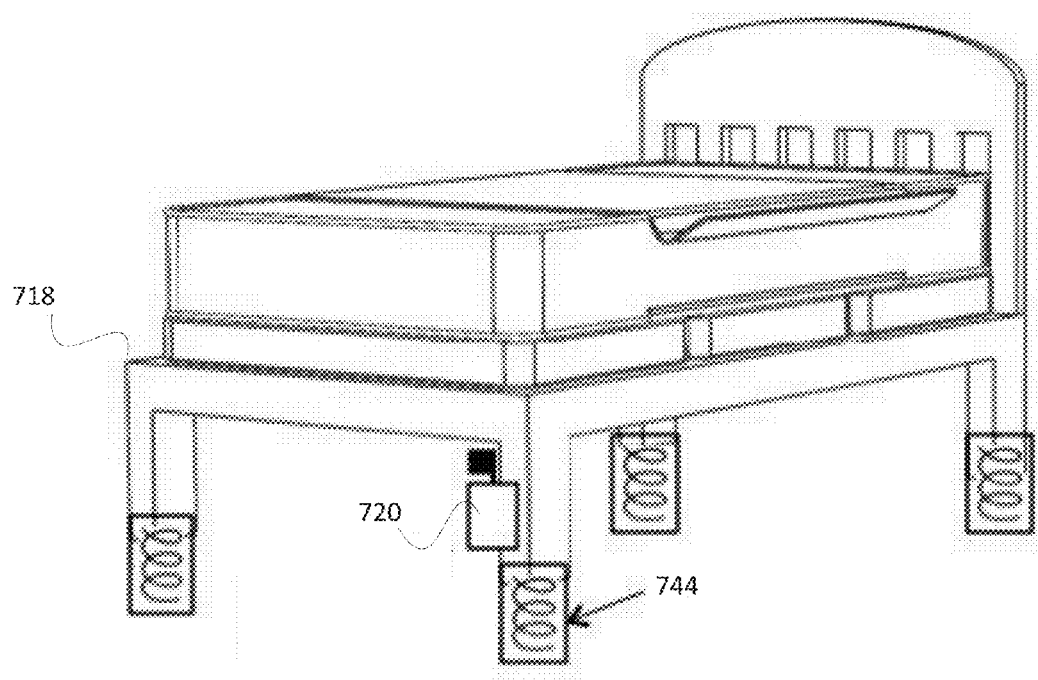
FIG. 7 shows a specific application of a vibration element in a sleep monitoring and therapeutic system.

In one specific embodiment, shown in FIG. 7, a bed frame 718 or crib can be raised on a plurality of springs or compliant members 744. The sleep monitoring and therapy module 720 can be attached to the bed frame 718 as described above. In some embodiments, multiple modules may be used. n another embodiment, the one or more sleep monitoring and therapy modules can include a plurality of vibrating motors with eccentric masses that are located at 180 degrees to each other can be used and rotated in opposite direction in order to ensure vibration along a single axis. The springs or compliant members 744 can improve the efficiency of vibration transfer from the sleep monitoring and therapy module to the bed frame, and thus to the user.

In some embodiments, the therapeutic device(s) of the sleep monitoring and therapeutic system comprise electrical stimulators for the application of electrical muscle stimulation (EMS) to awaken or partially awaken the user. EMS, also known as neuromuscular electrical stimulation (NMES) or electromyostimulation, is the elicitation of muscle contraction using electric impulses. The impulses can be generated by an EMS device and delivered through electrodes on the skin in direct proximity to the muscles to be stimulated. The intensity of the electrical stimulus can be titrated by adjusting a current level delivered through the electrical stimulator(s). Further, the intensity of the electrical stimulus can be titrated based on feedback from the sensors of the sleep monitoring and therapeutic system. The therapeutic device may deliver a stimulus to the brain, ear canal, nose, eyelid muscles, throat, head, hair, muscle, skin, etc. The stimulus may be targeted to tickle the patient or user, induce a cough or nausea, induce or simulate the urge to urinate, induce or simulate a bowel movement, etc. The therapeutic device may pass an electric current through the patient or user.

In some embodiments, the therapeutic device(s) of the sleep monitoring and therapeutic system comprise mechanisms configured to change or alter a temperature of the user or of the user's sleeping environment to awaken or partially awaken the user. Thus, the therapeutic device(s) can be configured to heat or cool the room, the bed, the pillow, the mattress, or the clothing of the user. Further the therapeutic devices can be configured to alternate between heating and cooling cycles. In some embodiments, the controller of the system includes metrics for the set temperatures, the rate of change of temperature, the duration of dwell at each set temperature, etc. Therapeutic devices can be configured to generate changes in temperature through the use of resistive heating, inductive heating, electric heating, chemical reactions, the use of thermoelectric materials, the introduction of warm or cool fluids, or any combination thereof.

In some embodiments, the therapeutic device(s) of the sleep monitoring and therapeutic system comprise visual stimulating devices, such as lights, projectors, or displays to awaken or partially awaken the user. The visual stimulation can include the use of bright light, colored light, focused light, or diffused light, or any combination thereof. Furthermore, the visual stimulation may be focused on the user's eyes. In some embodiments, the light can be modulated to mimic the effect of a TV on the eyes. The light may be modulated to gradually change in intensity and color so as to mimic the morning lights. In one embodiment, a video of the patient's parents may be played.

In some embodiments, the therapeutic device(s) of the sleep monitoring and therapeutic system comprise auditory devices or speakers configured to deliver a sound or auditory signal to the user to awaken or partially awaken the user. The auditory signal can comprise sounds associated with a television, radio, music, a parent's voice, a child's cry, loud distracting noises, the sound of city streets, the sounds of festivals such as Christmas, etc. Furthermore, the tone of the auditory signal delivered to the user may be changed in order to awaken the patient or user.

In a related embodiment, ear plugs may be placed in or on or around the patient's ear. The plugs may be configured to be automatically removed when it is time to awaken the patient. The plug may also include a microphone and amplifier that modulate the auditory signal level based on the required state of sleep.

In some embodiments, the therapeutic device(s) of the sleep monitoring and therapeutic system can be configured to mechanically move the patient or user to awaken or partially awaken the user. The mechanical movement can achieved by tilting or rocking the bed, mattress, and/or sleeping surface, firming or softening the sleeping surface or pillow, rolling the patient or user off the bed, or removing the covers off the patient or user, etc. In another embodiment, the stimulus may include a trapezius squeeze, a sternal rub, applying mandibular pressure, supraorbital pressure or squeezing the lunula area of the finger or toe nail, or any combination thereof.

Figure 8A:
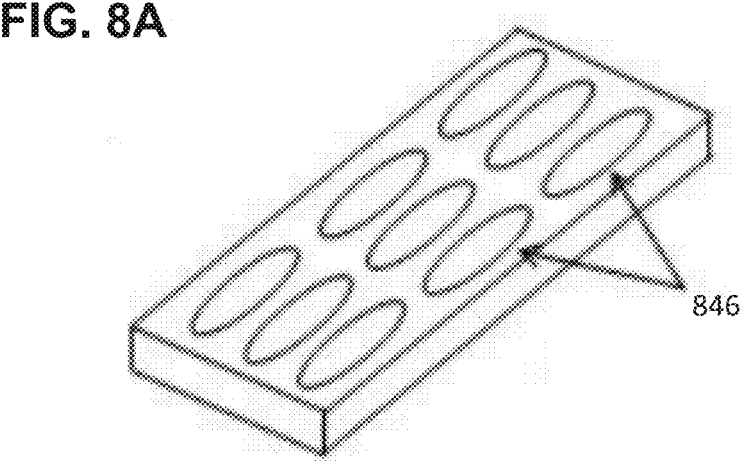
FIGS. 8A-8C show various embodiments of a sleep monitoring and therapeutic system configure to alter a topography of a sleeping surface of a user.
Figure 8B:
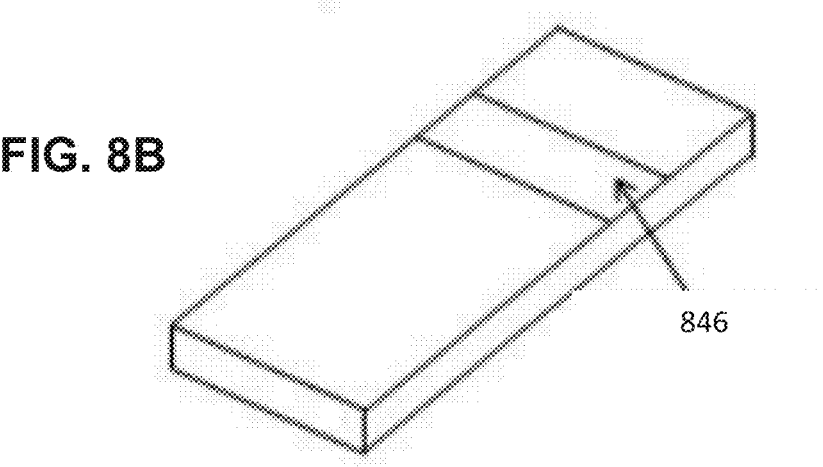
Figure 8C:
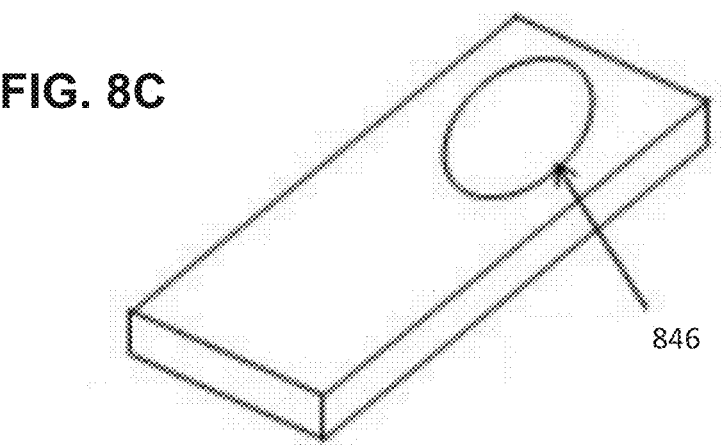

FIGS. 8A-8C illustrate one embodiment of a therapeutic device configured to alter the topography of a sleeping surface to awaken or partially awaken the user. In this embodiment, the therapeutic device can include a plurality of inflatable bladders 846 (FIG. 8A), a single inflatable bladder 846 extending across the sleeping surface (FIG. 8B), or a single inflatable bladder 846 confined to a specific region of the sleeping surface, such as under the head or torso of the user (FIG. 8C). The inflatable bladder therapeutic device can be configured to alter the topography of the sleeping surface by introducing and/or draining a fluid or gas into or from the inflatable bladder in order to inflate and/or deflate the sleeping surface. The inflatable bladder(s) can be sandwiched between a top padding layer and a bottom padding layer of a mattress pad, place on top of a mattress, placed below a mattress, or incorporated into the bed or crib.

The fluid or gas can be introduced into the inflatable bladders with pumps, compressors, compressed tanks, compressed reservoirs, or any similar methods and devices of transporting fluid or gas.

In another embodiment, the inflatable bladder(s) can be incorporated into a pillow, or placed inside a pillow case to change a topography of the surface under the user's head.

In some embodiments, the therapeutic device of the sleep monitoring and therapeutic system may be configured to inform others to awaken the user. For example, the therapeutic device may inform a parent or caregiver of the user. The therapeutic device can be configured to communicate with a caregiver of the user either in proximity to the user or off-site. The therapeutic device may be configured to communicate over mobile, telephonic, and data networks, or any combination thereof. For example, the therapeutic device can be configured to call, text, email, or otherwise alert another person to awaken the user. The therapeutic device may also be capable of communicating with a service animal, which is trained to awaken the patient or user.

In one embodiment, the sleep monitoring and therapeutic system is configured to communicate with a user, parent or caregiver in the instance that the desired therapeutic intervention is not achieved. In a specific embodiment, the device can alert the user, parent or caregiver in the instance that the child is not awakened during the intervention. In another embodiment, the device can alert the user, parent or caregiver in the instance that the user gets out of bed.

In another embodiment, the therapeutic devices may be configured to alter the breathing pattern of the patient or user to awaken or partially awaken the user, such as by obstructing the natural breathing orifices, stimulating the diaphragm through electrical pulse, etc.

In another embodiment, therapeutic device can be configured to apply a gustatory signal to awaken or partially awaken the user. The gustatory signal may be, for example, inducing a good and/or bad taste in the mouth. Therapeutic devices can be used to cause the patient or user to feel hungry or to salivate. In another embodiment, the therapeutic device may consist of a means to elevating the blood glucose level of the patient or user. The direct delivery of glucose or other food substances may be intravenous, per os, or per rectum, or any combination thereof. The therapeutic device may include a way to deliver an olfactory signal to the patient or user. The olfactory signal may comprise of, but not be limited to, the smell of coffee, hot sauce, smell salts, irritant smells, perfumes, etc.

In another embodiment, the therapeutic devices can be configured to induce a pharmacological or chemical reaction to awaken or partially awaken the user. A pharmacological or chemical agent may be delivered to the patient or user intravenous, per os, per rectum, transcutaneous, or any combination thereof. In another embodiment, an ingestible capsule may be capable of timed delivery of a pharmacological or chemical agent.

In yet another embodiment, the tears of the patient or user may react with other chemicals to initiate a reaction to awaken or partially awaken the user.

In another embodiment, the therapeutic device may comprise delivering a tactile signal to the user to awaken or partially awaken the user. The tactile signal may be delivered so as to tickle, poke, push, pull, or pinch the patient or user, or any combination thereof. The tactile signal may be delivered by contacting the patient or user or without contacting the patient or user, such as turning on a bedside fan or blowing air on the patient or user.

In another embodiment, the therapeutic device may be capable of increasing the moisture level or generating the sensation of moisture, in the vicinity or on the user to awaken or partially awaken the user.

In some embodiments, the therapeutic device can include the application of multiple stimuli to the user to awaken or partially awaken the user. The stimuli can include light, sound, thermal, vibrations, and motion, amongst others. The stimuli can be used in combination in order to achieve the defined end point for the therapeutic device. The stimuli used can also be customized to the user in order to achieve the defined end point. For example, a subset of the available stimuli can be used on an individual user if found to be most effective in achieving the end point.

The electronic controller of the sleep monitoring and therapeutic system can achieve partial arousal and/or partial awakening in the user by altering the amplitude, frequency, intensity, duty cycle or duration of the therapeutic intervention, or any combination thereof. For example, in a vibratory system based a drive voltage may be pulse-width modulated in order to increase or decrease the therapeutic intervention. In another example, a temperature of the sleep surface can be modulated in order to increase or decrease the therapeutic intervention. Further a control algorithm can be used to modulate the therapeutic intervention to achieve a partial arousal and/or partial awakening.

A closed loop control scheme generally includes a feedback control loop wherein the sensors provide feedback to the electronic controller (i.e., information obtained from one or more sensors monitoring various sleep parameters such as sleep stage, user motion, time of sleep onset, etc.). The controller can also receive input signals from the input controls of the user interface device. The controller can be configured to utilize the input signals and the sensed data to modulate the system. In some embodiments, the feedback control loop is a real-time feedback loop, and in other embodiments, the feedback control loop is an offline feedback loop. In another embodiment, the feedback control loop can incorporate a machine or computer learning algorithm to adjust future therapy parameters.

In one embodiment, the system can include a closed loop feedback based system to partially awaken a user but prevent the user from being fully awakened. In this embodiment, the one or more sensors can sense a sleep parameter of the user, such as sleep stage or state of the user, detection of sleep metrics, detection of either gross or micro bodily movement, and/or detection and monitoring of user vitals such as heart rate, body temperature, blood pressure, etc. The electronic controller can evaluate the sensed sleep parameter to determine a target awakening time. In some embodiments, the target awakening time can be manually entered. The electronic controller can direct the one or more therapeutic devices to automatically apply a therapeutic intervention (e.g., such as vibration, electrical stimulation, visual stimulation, auditory stimulation, etc.) to the user at the target awakening time. During, or after the application of the therapeutic intervention, the one or more sensors can continue to sense a sleep parameter of the user, and the electronic controller can monitor the sleep state of the user based on the sensed sleep parameter. The electronic controller can terminate the therapeutic intervention automatically when the monitoring of the sleep state of the user indicates that the user is partially awakened.

Information from the one or more sensors can be used to determine that the user is partially awakened. For example, force or motion sensors can indicate a degree of gross bodily movement associated with a partially awakening. Similarly, auditory sensors can be used to determine a partially awakening based on speech, cries, or sounds from the user. Electrical sensors, or heart rate sensors can be used to determine a partial awakening based on changes to vital signs of the user, such as an increased heart rate, respiratory rate, or EEG or EKG activity. By monitoring the user during the application of therapy, the controller can titrate the therapy and/or terminate the therapy while the user is partially awakened, preventing the user from reaching a fully awakened state.

In embodiments, the controller can execute a control algorithm comprising a software application residing in the memory and executable by the controller. The arousal threshold for each user can be different and the arousal threshold for each user can vary each night. The use of the monitoring system to modulate the therapeutic intervention can personalize the therapeutic intervention for each user, each night. Further, the controller can utilize sensor data to determine an end point for the therapeutic intervention each night.

In one embodiment, a control algorithm defines a state variable to express a real-time value of one or more properties of the user's sleep stage and/or one or more properties of the user's physiologic state. For example, the state variable can represent the real-time state of the user's sleep stage as Stage 1, Stage 2, Stage 3, Stage 4, Awake or REM. In another example, the state variable can represent the real-time state of the user's motion as "idle", "increasing", "decreasing", or "active." The active state can be defined as movement above a threshold for a specific period of time. The increasing and decreasing states can be defined based on changes in the magnitude of movement and/or the duration of movement.

In one embodiment, the state variable can be initially assigned to "idle" and the base therapeutic intervention can be initiated. Subsequently, the control algorithm can enter a loop wherein the algorithm monitors the state variable to be in either one of the two states, "active" or "idle". If the detected state of the state variable is "active", the algorithm can store the parameters of the successful therapeutic intervention and terminate the therapeutic intervention. If the detected state of the state variable is "idle", the algorithm can enter a therapeutic intervention modulation loop.

If the detected state of the state variable is "increasing", the parameters of the therapeutic intervention may remain unchanged and the therapeutic intervention is administered. If the detected state of the state variable is "decreasing" or "idle", the parameters of the therapeutic intervention can be modulated in order to increase the therapeutic intervention. For example, the therapeutic intervention can be increased through altering the amplitude, frequency, intensity, duty cycle or duration of the therapeutic intervention, or any combination thereof.

Further, once a successful therapeutic intervention is achieved, the parameters of that intervention can be used to define a new base therapeutic intervention for subsequent interventions. In a specific embodiment, the new base therapeutic intervention parameters can be set to the parameters of the successful intervention. In one embodiment, the new base therapeutic intervention parameters can be set between the current base therapeutic intervention parameters and the successful therapeutic intervention parameters.

In some embodiments, the control algorithm can be configured to initiate an external intervention in the event that the intervention by the therapeutic system does not meet the end point. For example, the controller can communicate with a caregiver. The caregiver can be instructed to initiate an intervention such as awakening the user. The communication with the caregiver can be via a wired controller, a wireless controller, a smart phone, etc.

Figure 9B:
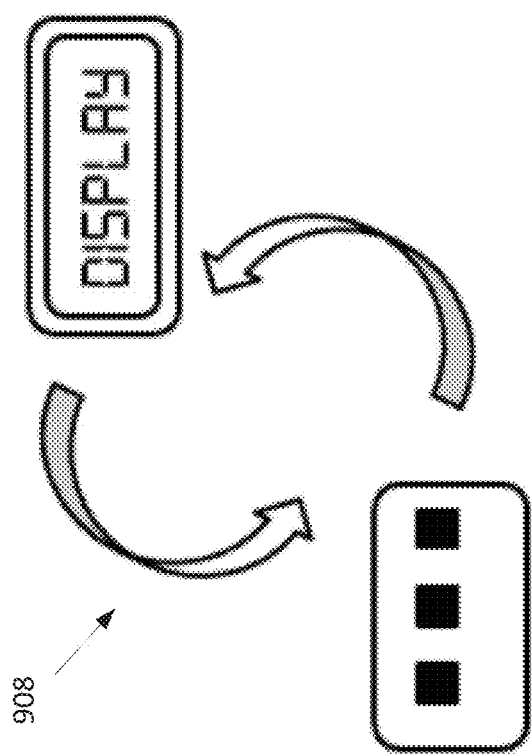
FIGS. 9A-9B show various embodiments of a user interface device of a sleep monitoring and therapeutic system.
Figure 9A:
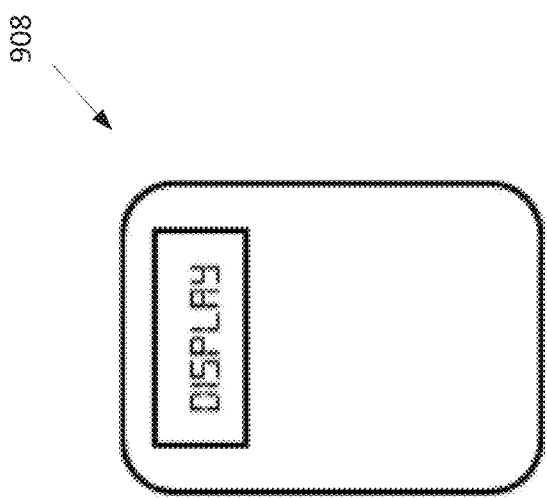

FIG. 9A-9B show two embodiments of a user interface device 908. The user interface device 908 can be configured to communicate with the sleep monitoring and therapeutic system and display information relating to the system, the data sensed from the user, and the therapy applied by the therapeutic device(s). The user interface device can comprise a smartphone, tablet, computer, television, wearable computer, watch, or other electronic device. The user or others can input information pertaining to the use of the sleep monitoring and therapeutic system via the user interface device. In some embodiments, the user interface device can be configured to transfer sleep and input parameters to an online database. The device can communicate through a wireless (WiFi, Bluetooth, BLE, Zigbee, etc.) or a wired connection.

In one embodiment, the sleep monitoring and therapeutic system can include a sleep diary feature that enables the user to keep a record of their sleep behavior. This allows the user to annotate their sleep data with other information that may provide further context around their sleep and sleep disorders. For example, the user may record the days they drank coffee and may in retrospect evaluate whether that impacted their sleep quality or the impact of an episode of a sleep disorder on their sleep quality. The user can update the sleep diary feature through the user interface device, for example.

In one embodiment, the therapeutic system can be used to aid the user in falling asleep. In one embodiment, the system can be used to aid the user in falling asleep during initial sleep onset or during any awakenings over the course of the user's sleep. In another embodiment, the system can be used to aid in returning the user to sleep after the therapeutic intervention. For example, in a vibratory system, the amplitude and frequency of the vibration may be gradually reduced in order to induce sleep. For example, in a system that alters the topography of the sleeping surface, the amplitude and frequency of the changes in the topography can be gradually reduced in order to induce sleep. Further, the system can turn off automatically after a preset duration in order to minimize any further disturbance of sleep. In another embodiment, the system may mimic the movement and motion of a car ride.

In another embodiment, the system can be used to improve sleep hygiene of the user. Sleep hygiene is the controlling of all behavioral and environmental factors that precede sleep and may interfere with sleep. The system can monitor of the daily activities, physiological parameters, stress levels, activity levels, nutritional intake, sleep environment, exposure to sunlight, or any combination thereof, in order to drive behavioral changes in the user and the care givers in order to improve the sleep hygiene of the user. The system can be worn over the duration of the entire day or a relevant portion of the day.

While the present disclosure is amenable to various modifications and alternative forms, specifics thereof have been shown by way of example in the drawings and will be described in further detail. It should be understood that the intention is not to limit the disclosure to the particular embodiments and/or applications described. Various embodiments described above and shown in the figures and attachments may be implemented together and/or in other manners. One or more of the items depicted in the drawings/figures can also be implemented in a more separated or integrated manner, as is useful in accordance with particular applications.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of treating sleep terrors in a user, comprising the steps of:
   providing a sleep therapy device including a vibrating element in contact with a sleeping surface of the user;
   determining, in the sleep therapy device, a target treatment time based on a time of occurrence of sleep terror episodes in the user; and
   causing a nonsustained arousal from sleep in the user in which the user does not reach a fully awakened state, without operator intervention, by automatically applying vibration therapy with the vibrating element of the sleep therapy device to the sleeping surface of the user at the target treatment time.

2. The method of claim 1, wherein the vibrating element is positioned under the sleeping surface or on the sleeping surface of the user.

3. The method of claim 1, wherein applying vibration therapy further comprises applying auditory stimulation to the user.

4. The method of claim 1 further comprising, prior to the determining step, sensing a sleep parameter of the user with the sleep therapy device.

5. The method of claim 4, wherein the sleep parameter comprises a sleep stage of the user.

6. The method of claim 4, wherein the sleep parameter comprises vital signs of the user.

7. The method of claim 4, wherein the sleep parameter comprises gross or micro bodily movement of the user.

8. The method of claim 4, wherein the sleep parameter comprises a sleep metric of the user.

9. The method of claim 1 wherein the target treatment time is determined from an average or median time of occurrence of sleep terror episodes.

10. The method of claim 1 wherein the target treatment time is determined from an elapsed time from sleep onset to the occurrence of sleep terror episodes.

11. The method of claim 1, wherein the determining step comprises inputting the target treatment time into the vibrating element.

12. The method of claim 1, wherein the determining step comprises inputting the target treatment time into an input device of the sleep therapy device.

13. A method of causing a nonsustained arousal from sleep in a user to treat sleep tenors in the user, comprising the steps of:
   determining a target awakening time in a therapy device;
   automatically applying vibration therapy with the therapy device to the user at the target awakening time without operator intervention;
   monitoring a sleep state of the user with the therapy device while applying an intervention; and
   preventing the user from reaching a fully awakened state by terminating the intervention automatically when the monitoring of the sleep state indicates that the user is partially aroused from sleep.

14. The method of claim 13, wherein the automatically applying step further comprises automatically applying the vibration therapy and an auditory sound with the therapy device to the user at the target awakening time without operator intervention.

15. An apparatus configured to partially arouse a user from sleep, comprising:
   an input interface configured to receive a target awakening time;
   at least one vibrating element configured to apply vibration therapy to a sleep surface of the user to partially awaken the user;
   at least one sensor configured to monitor a sleep parameter of the user; and
   a controller operatively coupled to the at least one vibrating element and the input interface, the controller configured to control the at least one vibrating element to apply the vibration therapy to the user at the target awakening time to partially arouse the user from sleep without allowing the user to reach a fully awakened state, wherein the controller is further configured to determine a sleep state of the user while the at least one vibrating element applies the vibration therapy to the user, and the controller is further configured to prevent the user from reaching the fully awakened state by terminating the vibration therapy when the user is partially aroused.

16. The apparatus of claim 15, further comprising an auditory device configured to apply an auditory sound to the user.

* * * * *